United States Patent [19]

Aoyama et al.

[11] Patent Number: 5,236,950

[45] Date of Patent: Aug. 17, 1993

[54] PROCESS FOR HAIR GROWTH

[75] Inventors: Hajime Aoyama; Satoshi Ono; Osamu Oohashi; Hirokazu Narita; Shuntaro Takano, all of Toyama, Japan

[73] Assignee: Toyama Chemical Co., Ltd., Tokyo, Japan

[21] Appl. No.: 311,945

[22] Filed: Feb. 17, 1989

[30] Foreign Application Priority Data

Feb. 18, 1988 [JP] Japan .................. 63-33968
Jun. 3, 1988 [JP] Japan ................. 63-136824

[51] Int. Cl.$^5$ ................................ A61K 7/06
[52] U.S. Cl. .................... 514/478; 514/354; 514/356; 514/532; 514/556; 514/715; 514/738; 514/739
[58] Field of Search .............. 514/70, 478, 556, 354, 514/356, 532, 715, 738

[56] References Cited

U.S. PATENT DOCUMENTS

| | | | |
|---|---|---|---|
| 4,139,619 | 2/1979 | Chidsey, III et al. | 424/45 |
| 4,192,953 | 3/1980 | Mishima et al. | 568/673 |
| 4,260,551 | 4/1981 | Mishima et al. | 260/410.6 |
| 4,346,109 | 8/1982 | Yamatsu et al. | 424/318 |
| 4,491,592 | 1/1985 | Katoh et al. | 424/318 |
| 4,596,812 | 6/1986 | Chidsey, III et al. | 514/256 |
| 4,738,801 | 4/1988 | Tahara et al. | 260/410.9 R |
| 4,939,171 | 7/1990 | Moeller et al. | 514/530 |

FOREIGN PATENT DOCUMENTS

| | | |
|---|---|---|
| 0129778 | 1/1985 | European Pat. Off. . |
| 0204586 | 12/1986 | European Pat. Off. . |
| 315913 | 11/1987 | European Pat. Off. . |
| 0287876 | 10/1988 | European Pat. Off. . |
| 1467925 | 1/1969 | Fed. Rep. of Germany . |
| 1467955 | 2/1969 | Fed. Rep. of Germany . |
| 2652256 | 6/1977 | Fed. Rep. of Germany . |
| 2812978 | 10/1979 | Fed. Rep. of Germany . |
| 3738405 | 5/1989 | Fed. Rep. of Germany . |
| 1190002 | 10/1959 | France . |
| 60-004113 | 10/1985 | Japan . |
| 61-207321 | 9/1986 | Japan . |
| 8302390 | 7/1983 | PCT Int'l Appl. . |
| 780801 | 8/1957 | United Kingdom . |
| 923400 | 4/1963 | United Kingdom . |
| 944834 | 12/1963 | United Kingdom . |
| 83/02390 | 7/1983 | World Int. Prop. O. . |

OTHER PUBLICATIONS

Derwent Abstract WPI Acc No. 75-62757W/38 (Takasago).
Derwent Abstract WPI Acc No. JP49069845 (Takasago).
Derwent-Ref: 60454Y/34 Nov. 1, 1976.
Derwent-Ref: 85-077293/13 Jul. 25, 1983.
Derwent-Ref: 85-077294/13 Jul. 28, 1983.
Derwent-Ref: 86-141951/22 Sep. 27, 1984.
Derwent-Ref: 62505B/34 Dec. 27, 1977.
Chemical Abstracts, vol. 83, p. 435, 1975, No. 65330r, Yoshigi Hideki, et al., "Cosmetics With Improved Moisture Retentivity".

*Primary Examiner*—Nicholas S. Rizzo
*Attorney, Agent, or Firm*—Oblon, Spivak, McClelland, Maier & Neustadt

[57] ABSTRACT

This invention relates to a hair-restorer comprising, as an active ingredient, (a) an acyclic branched higher aliphatic hydrocarbon of 20 carbon atoms which may be substituted with hydroxyl group or acyloxy group, or (b) an acyclic branched carboxylic acid of 20 carbon atoms or its derivative and to a process for hair growth.

38 Claims, No Drawings

PROCESS FOR HAIR GROWTH

This invention relates to a novel hair-restorer and a process for hair growth. More particularly, this invention relates to a hair-restorer comprising, as an active ingredient, a compound represented by the general formula [I]:

$$R^1—R^2 \quad [I]$$

wherein $R^1$ is an acyclic branched higher aliphatic hydrocarbon group of 20 carbon atoms which may be substituted with hydroxyl or acyloxy group, or an acyclic branched acyl group of 20 carbon atoms, and $R^2$ is a hydroxyl group or a substituted or unsubstituted alkoxy, alkylthio, alkylsulfinyl, alkylsulfonyl, carbamoyloxy or acyloxy group when $R^1$ is the former group, and is a hydroxyl group or a substituted or unsubstituted alkoxy group when $R^1$ is the latter group, or a pharmaceutically acceptable salt thereof and to a process for hair growth.

Hair-restorers conventionally comprise various effective ingredients. Known hair-restorers comprise, for example, amino acids such as serine, methionine and the like; vasodilators such as acetylcholine derivative and the like; anti-inflammatory agents such as salicylic acid, lithospermi radix extract and the like; hormone preparations such as estradiol and the like; vitamins such as vitamin E and the like; keratolytics; wetting agents; perfumes; dandruff-suppressing agents; refrigerants; crude drug extracts; and fatty acids.

Japanese Patent Application Kokai (Laid-Open) No. 4113/1985 describes, as an active ingredient for hair-restorer, an alcohol having an odd number of carbon atoms or its derivative. Japanese Patent Application Kokai (Laid-Open) No. 207321/1986 describes, as an active ingredient for hair-restorer, a higher aliphatic alcohol of 22-34 carbon atoms.

The conventional hair-restorers, however, do not have sufficient effect for hair restoration.

In view of the above situation, the present inventors have made research on substances having an excellent hair-restoration effect for alopecia without exhibiting any side effect. As a result, it has been found that the compounds represented by the general formula [I] or their pharmaceutically acceptable salts exhibit an excellent hair growth effect.

An object of this invention is to provide a hair-restorer comprising, as an active ingredient, a substance of excellent hair-restoration effect.

Another object of this invention is to provide a topical composition for application to mammalian (e.g. mice, sheep, rabbits, monkeys, minks, humans and the like) skin.

A further object of this invention is to provide a process for hair growth.

Other objects and advantages of this invention will become apparent from the following description.

According to this invention, there is provided a hair-restorer comprising, as an active ingredient, a compound represented by the general formula [I]:

$$R^1—R^2 \quad [I]$$

wherein $R^1$ and $R^2$ have the same meanings as defined above or a pharmaceutically acceptable salt thereof.

In the compound of the general formula [I], with respect to $R^1$, the acyclic branched higher aliphatic hydrocarbon group of 20 carbon atoms includes, for example, phytyl group (3,7,11,15-tetramethyl-2-hexadecen-1-yl group), isophytyl group (3,7,11,15-tetramethyl-1-hexadecen-3-yl group), geranyllinalyl group (3,7,11,15-tetramethylhexadecane-1,6,10,14-tetraen-3-yl group) and the like; the acyclic branched higher aliphatic hydrocarbon group of 20 carbon atoms substituted with hydroxyl group includes, for example, 7-hydroxymethyl-3,11,15-trimethylhexadecane-2,6,10,14-tetraen-1-yl, 2,3-dihydroxy-3,7,11,15-tetramethylhexadecanyl group and the like; the acyclic branched higher aliphatic hydrocarbon group of 20 carbon atoms substituted with acyloxy group includes the above acyclic branched higher aliphatic hydrocarbon groups substituted with the same acyloxy group as in the definition of $R^2$ to be described hereinafter, for example, 2,3-diacetoxy-3,7,11,15-tetramethylhexadecanyl group and the like; and the acyclic branched acyl group of 20 carbon atoms includes, for example, 3,7,11,15-tetramethyl-2-hexadecenoyl group and the like.

With respect to $R^2$, the alkoxy group includes, for example, $C_{1-8}$alkoxy groups such as methoxy, ethoxy, n-propoxy, isopropoxy, butoxy and the like, the alkylthio group includes $C_{1-8}$alkylthio groups such as methylthio, ethylthio, n-propylthio, isopropylthio, butylthio and the like; the alkylsulfinyl group includes $C_{1-8}$alkylsulfinyl groups such as methylsulfinyl, ethylsulfinyl, n-propylsulfinyl, isopropylsulfinyl, butylsulfinyl and the like; the alkylsulfonyl group includes $C_{1-8}$alkylsulfonyl groups such as methylsulfonyl, ethylsulfonyl, n-propylsulfonyl, isopropylsulfonyl, butylsulfonyl and the like, and the acyloxy group includes, $C_{2-20}$aliphatic acyloxy groups, for example, $C_{2-20}$alkanoyloxy groups such as acetyloxy, propionyloxy, butyryloxy, isobutyryloxy, isovaleryloxy, pivaloyloxy, lauroyloxy, palmitoyloxy, stearoyloxy and the like, $C_{3-20}$alkenoyloxy groups such as acryloyloxy and the like, $C_{3-20}$alkynoyloxy groups such as propioloyloxy and the like and $C_{3-7}$cycloalkylcarbonyloxy groups such as cyclopropylcarbonyloxy, cyclohexylcarbonyloxy and the like; aroyloxy groups such as benzoyloxy, naphthoyloxy and the like; and 5- or 6-membered heterocyclic carbonyloxy groups such as nicotinoyloxy, isonicotinoyloxy, 1,4-dihydropyridylcarbonyloxy, prolyloxy, thenoyloxy, furoyloxy and the like; the carbamoyloxy group includes, for example, carbamoyloxy group; N-$C_{1-8}$alkylcarbamoyloxy groups such as N-methylcarbamoyloxy, N-ethylcarbamoyloxy and the like; N,N-di-$C_{1-8}$alkylcarbamoyloxy groups such as N,N-dimethylcarbamoyloxy, N,N-diethylcarbamoyloxy and the like; and N-arylcarbamoyloxy groups such as N-phenylcarbamoyloxy and the like.

The above groups may have at least one substitutent selected from $C_{1-4}$alkyl groups such as methyl, ethyl, n-propyl, isopropyl and the like; $C_{3-7}$cycloalkyl groups such as cyclopropyl, cyclobutyl, cyclohexyl and the like; $C_{1-4}$alkoxy groups such as methoxy, ethoxy, n-propoxy, isopropoxy and the like; $C_{1-4}$alkylthio groups such as methylthio, ethylthio, n-propylthio, isopropylthio and the like; $C_{2-4}$acyloxy groups such as acetyloxy, propionyloxy, butyryloxy and the like; $C_{1-4}$alkylenedioxy groups such as methylenedioxy, ethylenedioxy and the like; hydroxyl group; aryl groups such as phenyl, 3-nitrophenyl, naphthyl and the like; carboxyl group; $C_{1-4}$alkoxycarbonyl groups such as methoxycarbonyl, ethoxycarbonyl and the like; amino group; $C_{1-4}$alkylamino groups such as methylamino, ethylamino and the like; di-($C_{1-4}$alkyl)amino groups such as dimethylamino, diethylamino, methylethylamino and the like; and tri-($C_{1-4}$alkyl)ammonio groups such as trimethylammonio, triethylammonio and the like.

Of these substituents, the hydroxyl group, the carboxyl group, the amino group, the alkylamino groups, etc. may be protected by, for example, the conventional protective groups described in, for example, Protective Groups in Organic Synthesis, Theodra W. Green, John Wiley & Sons, Inc.

The salt of the compound of the general formula [I] may be any pharmaceutically acceptable salt, and includes, for example, salts with alkali metals (e.g. sodium, potassium and the like), alkaline earth metals (e.g. magnesium, calcium and the like), organic bases (e.g. triethylamine, pyridine and the like), mineral acids (e.g. hydrochloric acid, sulfuric acid and the like) and sulfonic acids (e.g. benzenesulfonic acid, toluenesulfonic acid, methanesulfonic acid and the like).

Next, the processes for producing the compound of the general formula [I] are described.

PROCESS (1)

The compound represented by the general formula [Ia] or a pharmaceutically acceptable salt thereof:

$$R^{1a}-R^{2a} \qquad [Ia]$$

wherein $R^{1a}$ is the same acyclic branched higher aliphatic hydrocarbon group of 20 carbon atoms as in the definition of $R^1$, and $R^{2a}$ is the same substituted or unsubstituted acyloxy group as in the definition of $R^2$, can be obtained by reacting a compound represented by the general formula [Ib]:

$$R^{1a}-OH \qquad [Ib]$$

wherein $R^{1a}$ has the same meaning as defined above or a salt thereof, with a compound represented by the general formula [II]:

$$R^{2a}-H \qquad (II)$$

wherein $R^{2a}$ has the same meaning as defined above or a reactive derivative in the carboxyl group thereof.

The salt of the compound of the general formula [Ib] includes, for example, salts with alkali metals such as sodium, potassium and the like.

The reactive derivative in the carboxyl group of the compound of the general formula [II] includes, for example, acid halides, active acid amides, active esters, acid anhydrides, mixed acid anhydrides and the like.

The use of a conventional dehydration-condensing agent such as dicyclohexylcarbodiimide or the like is preferable when the compound of the general formula [II] is used. When the reactive derivative in the carboxyl group of the compound of the general formula [II] is used, it is preferable to use an inorganic or organic base such as sodium hydride, pyridine, triethylamine or the like.

The above reaction may be effected in a solvent, and the solvent to be used can be any solvent as long as it does not adversely affect the reaction, and includes, for example, aromatic hydrocarbons such as benzene, toluene and the like; halogenated hydrocarbons such as methylene chloride, chloroform and the like; ethers such as tetrahydrofuran, dioxane and the like; pyridine; amides such as hexamethylphosphorictriamide, N,N-dimethylformamide, N,N-dimethylacetamide and the like; and sulfoxides such as dimethyl sulfoxide and the like. These solvents can be used alone or in admixture of two or more.

In the above reaction, the compound of the general formula [II] or the reactive derivative in the carboxyl group thereof is used in an amount of at least 1 mole per mole of the compound of the general formula [Ib] or the salt thereof. The dehydration-condensing agent or the base is used in an amount of at least 1 mole per mole of the compound of the general formula [Ib] or the salt thereof.

The above reaction can be effected ordinarily at 0°–80° C. for 10 minutes to 10 hours.

PROCESS (2)

The compound of the general formula [Ia] or a pharmaceutically acceptable salt thereof can be obtained by reacting a compound represented by the general formula [III]:

$$R^{1a}-X \qquad [III]$$

wherein $R^{1a}$ has the same meaning as defined above and X is a removable group, with the salt of the compound of the general formula [II].

The removable group X includes, for example, halogen atoms such as fluorine, chlorine, bromine, iodine and the like; $C_{1-4}$alkanesulfonyloxy groups such as methanesulfonyloxy, ethanesulfonyloxy and the like; and arenesulfonyloxy groups such as toluenesulfonyloxy, benzenesulfonyloxy and the like.

The salt of the compound of the general formula [II] includes salts with alkali metals such as sodium, potassium and the like.

The above reaction may be effected in a solvent, and the solvent to be used can be any solvent as long as it does not adversely affect the reaction, and includes the same solvents as in the process (1).

In the above reaction, the salt of the compound of the general formula [II] is used in an amount of at least 1 mole per mole of the compound of the general formula [III].

The above reaction can be effected ordinarily at −70°–150° C. for 10 minutes to 20 hours.

PROCESS (3)

The compound represented by the general formula [Ic] or a pharmaceutically acceptable salt thereof:

$$R^{1a}-R^{2b} \qquad [Ic]$$

wherein $R^{1a}$ has the same meaning as defined above and $R^{2b}$ is the same substituted or unsubstituted alkoxy or alkylthio group as in the definition of $R^2$, can be obtained by reacting a compound represented by the general formula [III]:

$$R^{1a}-X \qquad [III]$$

wherein $R^{1a}$ and X have the same meanings as defined above, with a salt of a compound represented by the general formula [IV]:

$$R^{2b}-H \qquad [IV]$$

wherein $R^{2b}$ has the same meaning as defined above.

The salt of the compound of the general formula [IV] includes, for example, salts with alkali metals such as sodium, potassium and the like, and salts with organic bases such as triethylamine, pyridine and the like.

The above reaction may be effected in a solvent, and the solvent to be used can be any solvent as long as it does not adversely affect the reaction, and includes, for example, aromatic hydrocarbons such as benzene, toluene and the like; halogenated hydrocarbons such as methylene chloride, chloroform and the like; ethers such as tetrahydrofuran, dioxane and the like; pyridine; amides such as hexamethylphosphorictriamide, N,N-dimethylformamide, N,N-dimethylacetamide and the like; and sulfoxides such as dimethyl sulfoxide and the like. These solvents can be used alone or in admixture of two or more.

In the above reaction, the salt of the compound of the general formula [IV] is used in an amount of at least 1 mole per mole of the compound of the general formula [III].

The above reaction can be effected ordinarily at 0°–80° C. for 10 minutes to 10 hours.

PROCESS (4)

The compound represented by the general formula [Id] or a pharmaceutically acceptable salt thereof:

$$R^{1a}-R^{2c} \qquad [Id]$$ 

wherein $R^{1a}$ has the same meaning as defined above and $R^{2c}$ is the same substituted or unsubstituted alkylsulfinyl or alkylsulfonyl group as in the definition of $R^2$, can be obtained by reacting a compound represented by the general formula [Ie] or a pharmaceutically acceptable salt thereof:

$$R^{1a}-R^{2d} \qquad [Ie]$$ 

wherein $R^{1a}$ has the same meaning as defined above and $R^{2d}$ is the same substituted or unsubstituted alkylthio group as in the definition of $R^2$, with 1 or 2 equivalents of an oxidizing agent to produce a corresponding sulfinyl compound (sulfoxide) or sulfonyl compound (sulfone).

The above reaction may be effected in a solvent, and the solvent to be used can be any solvent as long as it does not adversely affect the reaction. It includes, for example, aromatic hydrocarbons such as benzene, toluene and the like; halogenated hydrocarbons such as methylene chloride, chloroform and the like; pyridine; amides such as hexamethylphosphorictriamide, N,N-dimethylformamide, N,N-dimethylacetamide and the like; and sulfoxides such as dimethyl sulfoxide and the like; etc. These solvents can be used alone or in admixture of two or more.

The oxidizing agent to be used in the above reaction includes, for example, inorganic oxidizing agents such as potassium permanganate, potassium periodate and the like and organic oxidizing agents such as peracetic acid, benzoyl peroxide and the like.

The above reaction can be effected ordinarily at 0°–80° C. for 10 minutes to 10 hours.

PROCESS (5)

The compound represented by the general formula [If] or a pharmaceutically acceptable salt thereof:

$$R^{1a}-R^{2e} \qquad [If]$$ 

wherein $R^{1a}$ has the same meaning as defined above and $R^{2e}$ is the same substituted or unsubstituted carbamoyloxy group as in the definition of $R^2$ can be obtained by reacting a compound represented by the general formula [Ib]

$$R^{1a}-OH \qquad [Ib]$$ 

wherein $R^{1a}$ has the same meaning as defined above, with a cyanate, a substituted isocyanate or a substituted carbamoyl halide.

The cyanate to be used in the above reaction includes, for example, sodium cyanate, potassium cyanate, etc. The substituted isocyanate includes, for example, $C_{1-4}$alkylisocyanates such as methylisocyanate, ethylisocyanate, propylisocyanate and the like; arylisocynates such as phenylisocyanate and the like; etc. The substituted carbamoyl halide includes, for example, $C_{1-4}$alkylsubstituted carbamoyl halides such as N-methylcarbamoyl chloride, N-ethylcarbamoyl chloride and the like; di-$C_{1-4}$alkyl-substituted carbamoyl halides such as N,N-dimethylcarbamoyl chloride, N-ethyl-N-methylcarbamoyl chloride, N,N-diethylcarbamoyl chloride and the like; etc.

The above reaction may be effected in a solvent, and the solvent to be used can be any solvent as long as it does not adversely affect the reaction, and includes the same solvents as in the process (3).

In the above reaction, the cyanate, the substituted isocyanate or the substituted carbamoyl halide is used in an amount of at least 1 mole per mole of the compound of the general formula [Ib].

The above reaction can be effected ordinarily at 0°–100° C. for 10 minutes to 20 hours.

PROCESS (6)

The compound represented by the general formula [Ig] or a pharmaceutically acceptable salt thereof:

$$R^{1b}-R^{2f} \qquad [Ig]$$ 

wherein $R^{1b}$ is the same acyclic branched acyl group 0f 20 carbon atoms as in the definition of $R^1$, and $R^{2f}$ is the same substituted or unsubstituted alkoxy group as in the definition of $R^2$, can be obtained by reacting a compound represented by the general formula [Ih]:

$$R^{1b}-OH \qquad [Ih]$$ 

wherein $R^{1b}$ has the same meaning as defined above or a reactive derivative in the carboxyl group thereof, with a compound represented by the general formula [V]:

$$R^{2f}-H \qquad [V]$$ 

wherein $R^{2f}$ has the same meaning as defined above or a salt thereof.

The salt of the compound of the general formula [V] includes, for example, salts with alkali metals such as sodium, potassium and the like.

The reactive derivative in the carboxyl group of the compound of the general formula [Ih] includes, for example, acid halides, active acid amides, active esters, acid anhydrides and mixed acid anhydrides and the like.

When the compound of the general formula [Ih] is used, it is preferable to use a conventional dehydration-condensing agent such as dicyclohexylcarbodiimide or the like. When the reactive derivative in the carboxyl group of the compound of the general formula [Ih] is used, it is preferable to use an inorganic or organic base such as sodium hydride, pyridine, triethylamine, 4-(N,N-dimethylamino)pyridine or the like.

The reaction may be effected in a solvent, and the solvent to be used can be any solvent as long as it does not adversely affect the reaction, and includes the same solvents as in the process (3).

In the above reaction, the compound of the general formula [V] or a salt thereof is used in an amount of at least 1 mole per mole of the general formula [Ih] or the reactive derivative in the carboxyl group thereof. When the dehydration-condensing agent or the base is used, the amount thereof is at least one mole per mole of the compound of the general formula [V] or a salt thereof.

The reaction can be effected ordinarily at −70° to 150° C. for 10 minutes to 20 hours.

The compound obtained in any of the above processes is subjected to removal of protective group by a conventional method and then purified by a conventional means such as column separation, distillation or the like.

When the compound of the general formula [I] and the pharmaceutically acceptable salt thereof have isomers (e.g. optical isomer, geometrical isomer, tautomeric isomer, etc.), this invention includes all the isomers, and also all crystal forms and solvates.

The content of the compound of the general formula [I] or the pharmaceutically acceptable salt thereof in the hair-restorer of this invention is not critical; however it is preferably 0.1–10% by weight, more preferably 0.5–5% by weight.

The hair-restorer of this invention may contain, to such an extent that its effect is not impaired, at least one member selected from various additives conventionally used in hair-restorers, such as amino acids (e.g. serine, methionine), hormone preparations (e.g. progesterone, estradiol), anti-inflammatory agents (e.g. lithospermi radix extract, glycyrrhethinic acid, hydrocortisone acetate), vasodilators (e.g. nicotinic acid, Minoxidil), crude drug extracts (e.g. Japanese chirata extract, carrot extract), dandruff-suppressing agents (e.g. hinokitiol, sulfur), refrigerants (e.g. l-menthol, camphor), wetting agents (e.g. glycerine, mucopolysaccharides, pyrrolidonecarboxylic acid), keratolytics (e.g. urea, resorcin), perfumes (e.g. lavender oil, neroli, bergamot), vitamin A, vitamin E, vitamine E derivatives, vitamine B6, vitamin H, lecithin, fatty acids and the like.

As the base of the hair-restorer of this invention, there can be used, for example, purified water, monohydric alcohols (e.g. ethanol, isopropyl alcohol), polyhydric alcohols (e.g. glycerine, propylene glycol), higher fatty acids (e.g. palmitic acid, linoleic acid), fats and oils (e.g. fatty acid glyceride, olive oil, squalene, bees wax), liquid paraffin, surfactants (e.g. polyoxyethylene hardened castor oil, stearyltrimethylammonium chloride, distearyldimethylammonium chloride, sodium laurylsulfate), emulsifiers (cetyl alcohol) and solubilizing agents.

The hair-restorer of this invention can be prepared in various forms such as powder, jellies, hair rinse, hair tonic, hair cream, hair lotion, hair spray, hair aerosol and the like.

Next, the effect of the hair-restorer of this invention is described.

TEST FOR HAIR GROWTH EFFECT

A group of 4 or 5 male $BDF_1$ mice (six weeks old) were shaved at the back to buttocks with a safety razor. For one week from the next day of the shaving, 0.2 ml/mouse of an ethanol solution containing 1% by weight or 2% by weight of testosterone (1% in the test in Table 1 and 2% in the test in Table 2) was applied to the shaved portion of each mouse once a day in order to suppress hair restoration. For 3 weeks from the 8th day after the shaving, 0.2 ml/mouse of the same solution was applied twice per week.

Meanwhile, 0.2 ml/mouse of each test solution was applied once a day for 3 weeks (excluding Sundays) from the 8th day after the shaving. In control group, 0.2 ml/mouse of a solution consisting of 85.5 parts by weight of ethanol, 10.0 parts by weight of glycerine and 4.5 parts by weight of purified water (this solution is hereinafter referred to as Solution A) was applied once a day for 3 weeks (excluding Sunday) from the 8th day after the shaving.

The extent of hair restoration was observed visually every day and hair-restoration effect was determined based on the number of the mice in which hair had been restorated completely on throughout the surface of the shaved portion.

Hair-restoration effect = (Number of mice in which hair had been restored completely)/(Number of tested mice)

In Tables 1 and 2 which appear hereinafter, hair-restoration effects in 2 weeks and 3 weeks from the application of test solution are shown.

Each test solution was prepared by incorporating each compound in Table 1 or 2 into Solution A at a concentration as shown in Table 1 or 2.

TABLE 1

| Test solution | | Hair-restoration effect | |
|---|---|---|---|
| Test compound | Concentration (%)** | After 2 weeks | After 3 weeks |
| Phytol | 3 | 0/5 | 5/5 |
| Isophytol | 3 | 0/5 | 4/5 |
| Phytantriol | 3 | 0/5 | 5/5 |
| Reference compound* | 3 | 0/5 | 0/5 |
| Solution A | — | 0/5 | 0/5 |

Notes:
*1-pentadecanoylglycerol
**wt. % based on total weight of the test solution

TABLE 2

| Test solution | | Hair-restoration effect | |
|---|---|---|---|
| No. of Reference Example | Concentration (%)** | After 2 weeks | After 3 weeks |
| 1 | 3 | 0/4 | 4/4 |
| 2 | 3 | 0/4 | 4/4 |
| 3 | 3 | 0/4 | 4/4 |
| 6 | 3 | 0/4 | 3/4 |
| 7 | 3 | 0/4 | 4/4 |
| 9 | 3 | 0/4 | 3/4 |
| 10 | 3 | 0/4 | 4/4 |
| 18 | 3 | 0/4 | 4/4 |
| 20 | 3 | 0/4 | 4/4 |
| 22 | 3 | 0/4 | 4/4 |
| 24 | 3 | 0/4 | 4/4 |
| 28 | 3 | 0/4 | 3/4 |
| 29 | 3 | 0/4 | 3/4 |
| 30 | 3 | 0/4 | 3/4 |
| 31 | 3 | 0/4 | 3/4 |
| 32 | 3 | 0/4 | 3/4 |
| 33 | 3 | 0/4 | 3/4 |
| 37 | 3 | 0/4 | 3/4 |
| 38 | 3 | 0/4 | 4/4 |
| 39 | 3 | 0/4 | 3/4 |
| Reference compound* | 3 | 0/4 | 0/4 |

TABLE 2-continued

| Test solution | | Hair-restoration effect | |
|---|---|---|---|
| No. of Reference Example | Concentration (%)** | After 2 weeks | After 3 weeks |
| Solution A | — | 0/4 | 0/4 |

Notes:
*1-Pentadecanoylglycerol
**wt. % based on total weight of the test solution.

As is clear from the above results, the hair-restorer of this invention exhibits an excellent hair-restoration effect.

Next, the process for producing the compound of the general formula [I] or its pharmaceutically acceptable salt of this invention is described in more detail referring to Reference Examples.

In the Reference Examples, the mixing ratios of mixed solvents are all by volume, and the carrier used in column chromatography is Kieselgel 60 Art. 7734 (a silica gel produced by Merck Co.) unless otherwise specified.

REFERENCE EXAMPLE 1

To a mixture consisting of 10 0 g of phytol, 9.0 g of triethylamine and 50 ml of methylene chloride was added 7.2 g of nicotinic chloride at 30°–40° C. The resulting mixture was stirred for 2 hours at the same temperature. After the completion of the reaction, the reaction mixture was washed with dilute hydrochloric acid, 3% aqueous sodium hydrogencarbonate solution and water in this order and then dried over anhydrous magnesium sulfate. The solvent was removed by distillation under reduced pressure. The residue obtained was purified by a column chromatography (eluant; n-hexane:ethyl acetate=9:1) to obtain 12.1 g (yield: 90%) of oily phytyl nicotinate.

IR (neat) $cm^{-1}$: 2920, 2850, 1725.

NMR ($CDCl_3$) δ value: 0.86 (12H, d, J=5.5Hz), 0.99–1.65 (19H, m), 1.76 (3H, s), 1.70–2.25 (2H, m), 4.87 (2H, d, J=7.0Hz), 5.48 (1H, t, J=6.4Hz), 7.33, 7.40 (1H, dd, J=7.9Hz, J=4.6Hz), 8.22, 8.35 (1H, dt, J=4.6Hz, J=1.9Hz), 8.74, 8.77 (1H, dd, J=4.6Hz, J=1.9Hz), 9.23 (1H, d, J=1.9Hz).

In the same manner, the compounds of Table 3 were obtained.

TABLE 3

| No. of Reference Example | Name of compound | IR (neat) $cm^{-1}$: | NMR ($CDCl_3$) δ value: |
|---|---|---|---|
| 2 | Phytyl propionate | 2920, 2850, 1740 | 0.86(12H, d, J=5.6Hz), 1.09(3H, s), 1.00–1.60(19H, m), 1.69(3H, s), 1.80–2.28(2H, m), 2.28–2.88(2H, m), 4.58(2H, d, J=7Hz), 5.34(1H, t, J=6.4Hz) |
| 3 | Phytyl isobutyrate | 2920, 2850, 1737 | 0.87(12H, d, J=5.6Hz), 1.00–1.65(25H, m), 1.69(3H, s), 1.80–2.60(3H, m), 4.59(2H, d, J=7Hz), 5.40(1H, t, J=6.8Hz) |
| 4 | Monophytyl succinate | 2910, 2850, 1735 | 0.86(12H, d, J=5.5Hz), 1.00–1.60(19H, m), 1.68(3H, s), 1.85–2.40(2H, m), 2.64(4H, s), 4.61(2H, d, J=7.3Hz), 5.34(1H, t, J=6.5Hz), 10.50(1H, s) |
| 5 | Phytyl 3, 4-methylenedioxy-benzoate | 2920, 2850, 1715 | 0.86(12H, d, J=5.5Hz), 0.99–1.55(19H, m), 1.74(3H, s), 1.70–2.20(2H, m), 4.79(2H, d, J=7.0Hz), 5.45(1H, t, J=6.4Hz), 5.98(2H, s), 6.78(1H, d, J=8.2Hz), 7.45(1H, d, J=1.5Hz), 7.63, 7.65(1H, dd, J=8.2Hz, J=1.5Hz) |
| 6 | Phytyl 3,4,5-trimethoxy-benzoate | 2920, 2850, 1715 | 0.86(12H, d, J=5.5Hz), 1.00–1.55(19H, m), 1.77 (3H, s), 1.70–2.20(2H, m), 3.89(9H, s), 4.83 (2H, d, J=7.0Hz), 5.47(1H, t, J=6.4Hz), 7.31 (2H, s) |
| 7 | Phytyl acetate | 2920, 2860, 1742 | 0.86(12H, d, J=5.5Hz), 0.99–1.55(19H, m), 1.69 (3H, s), 1.76–2.20(2H, m), 2.02(3H, s), 4.58 (2H, d, J=7.0Hz), 5.34(1H, t, J=6.4Hz) |
| 8 | 3-phytyl-5-ethyl 2,6-dimethyl-4-(3-nitrophenyl)-1,4-dihydro-pyridine-3,5-dicarboxylate | 3320, 2910, 2840, 1690, 1670 | 0.86(12H, d, J=5.6Hz), 1.00–1.55(22H, m), 1.62 (3H, s), 1.76–2.20(2H, m), 2.32(6H, s), 3.80–4.30(2H, m), 4.52(2H, d, J=6.1Hz), 5.05–5.40 (2H, m), 6.71(1H, bs), 7.10–8.20(3H, m) |
| 9 | Phytyl acetyllactate | 2920, 2840, 1750 | 0.87(12H, d, J=5.6Hz), 1.00–1.50(19H, m), 1.61 (3H, d, J=7.0Hz), 1.70(3H, s), 1.80–2.30(2H, m), 2.11(3H, s), 4.65(2H, d, J=7.3Hz), 5.00–5.70(2H, m) |
| 10 | Phytyl pivalate | 2900, 2840, 1720 | 0.88(12H, d, J=5.5Hz), 1.00–1.82(28H, m), 1.69 (3H, s), 1.92–2.16(2H, m), 4.58(2H, d, J=7.0Hz), 5.34(1H, t, J=6.4Hz) |
| 11 | Phytyl isovalerate | 2910, 2840, 1725 | 0.60–1.04(18H, m), 1.04–1.62(20H, m), 1.69(3H, s), 1.93–2.80(4H, m), 4.58(2H, d, J=7.0Hz), 5.35 (1H, t, J=6.4Hz) |
| 12 | Phytyl cyclohexylcarboxylate | 2910, 2840, 1727 | 0.86(12H, d, J=5.5Hz), 1.00–2.60(35H, m), 4.56 (2H, d, J=7.0Hz), 5.34(1H, t, J=7.0Hz) |
| 13 | phytyl cyclohexylacetate | 2900, 2840, 1727 | 0.86(12H, d, J=5.5Hz), 1.00–2.20(37H, m), 4.57 (2H, d, J=7.0Hz), 5.34(1H, t, J=7.0Hz) |
| 14 | Phytyl ethoxypropionate | 2920, 2850, 1755 | 0.86(12H, d, J=5.5Hz), 1.00–1.63(24H, m), 1.71 (3H, s), 1.85–2.30(2H, m), 3.59(2H, q, J=7.0Hz), 4.04(2H, s), 4.66(2H, d, J=7.3Hz), 5.36(1H, t, J=6.4Hz) |

TABLE 3-continued

| No. of Reference Example | Name of compound | IR (neat) cm$^{-1}$: | NMR (CDCl$_3$) δ value: |
|---|---|---|---|
| 15 | Monophytyl maleate | 2920, 2850, 1720 | 0.86(12H, d, J=5.6Hz), 1.00–1.60(19H, m), 1.69 (3H, s), 1.80–2.28(2H, m), 4.79(2H, d, J=7.0Hz), 5.34(1H, t, J=6.4Hz), 6.29(2H, s), 10.06 (1H, s) |
| 16 | Methyl phytyl succinate | 2910, 2850, 1730 | 0.86(12H, d, J=5.5Hz), 1.01–1.60(19H, m), 1.68 (3H, s), 1.80–2.15(2H, m), 2.61(4H, s), 3.68 (3H, s), 4.61(2H, d, J=7.0Hz), 5.34(1H, t, J=7.1Hz) |
| 17 | Isophytyl acetate | 2920, 2850, 1735 | 0.86(12H, d, J=5.5Hz), 1.00–1.80(24H, m), 2.09 (3H, s), 5.00–5.50(2H, m), 5.80–6.50(1H, m) |
| 18 | Phytyl formyllactate | 2920, 2850, 1750 | 0.86(12H, d, J=5.5Hz), 1.00–1.50(19H, m), 1.55 (3H, d, J=7.0Hz), 1.70(3H, s), 1.80–2.30(2H, m), 4.65(2H, d, J=7.3Hz), 5.00–5.70(2H, m), 8.06(1H, s) |

REFERENCE EXAMPLE 19

10 ml of a methylene chloride solution containing 10.0 g of chloroacetylmandelic acid chloride was dropped into a solution of 10.0 g of phytol and 4.5 g of triethylamine dissolved in 30 ml of methylene chloride at 30°–40° C. The resulting mixture was stirred for 2 hours at the same temperature. After the completion of the reaction, the reaction mixture was washed with dilute hydrochloric acid, 3% aqueous sodium hydrogencarbonate solution and water in this order. The solvent was removed by distillation under reduced pressure. The residue obtained was dissolved in 50 ml of methanol. Thereto were added 3.8 g of triethylamine and 2.9 g of thiourea at room temperature. The resulting mixture was stirred for 3 hours at the same temperature. After the completion of the reaction, the solvent was removed by distillation under reduced pressure. The residue obtained was dissolved in ethyl acetate and the resulting solution was washed with dilute hydrochloric acid, 3% aqueous sodium hydrogencarbonate solution and water in this order and then dried over anhydrous magnesium sulfate. The solvent was removed by distillation under reduced pressure. The residue obtained was purified by a column chromatography (eluant; n-hexane:ethyl acetate=9:1) to obtain 13.0 g (yield: 90%) of oily phytyl mandelate.

IR (neat) cm$^{-1}$: 3500, 2920, 2850, 1730.

NMR (CDCl$_3$) δ value: 0.86 (12H, d, J=5.5Hz), 0.99–1.55 (19H, m), 1.60 (3H, s), 1.70–2.20(2H, m), 3.64 (1H, bs), 4.64 (2H, d, J=7.3Hz), 5.14 (1H, s), 5.27 (1H, t, J=7.0Hz), 7.10–7.55 (5H, m).

REFERENCE EXAMPLE 20

Phytyl lactate was obtained in the same manner as in Reference Example 19.

IR (neat) cm$^{-1}$: 3450, 2920, 2860, 1730.

NMR (CDCl$_3$) δ value: 0.86 (12H, d, J=5.4Hz), 1.00–1.60 (22H, m), 1.69 (3H, s), 1.85–2.30 (2H, m), 4.10–4.50 (1H, m), 4.68 (2H, d, J=6.8Hz), 5.35 (1H, t, J=6.8Hz).

REFERENCE EXAMPLE 21

10.0 g of bromophytyl was added to a solution of 6.4 g of sodium nicotinate dissolved in 40 ml of N,N-dimethylformamide. The resulting mixture was stirred for 15 hours at 60° C. After the completion of the reaction, the reaction mixture was concentrated under reduced pressure. The residue obtained was dissolved in n-hexane. The solution was washed with dilute hydrochloric acid, 3% aqueous sodium hydrogencarbonate solution and water in this order and then dried over anhydrous magnesium sulfate. The solvent was removed by distillation under reduced pressure. The residue obtained was purified by a column chromatography (eluant; n-hexane:ethyl acetate=9:1) to obtain 8.4 g (yield: 75%) of oily phytyl nicotinate.

The properties (IR and NMR) of this compound were identical with those of the compound obtained in Reference Example 1.

REFERENCE EXAMPLE 22

A solution of 4.74 g of N-acetylglycine and 12.36 g of 4-(N,N-dimethylamino)pyridine dissolved in 70 ml of methylene chloride was cooled to −50° C. Thereinto was dropped 4.25 g of methanesulfonyl chloride. After the completion of the dropping, the resulting mixture was stirred at the same temperature for 1 hour. Thereinto was dropped 10.00 g of phytol at the same temperature, after which the temperature of the mixture was elevated to room temperature in 6 hours. After completion of the reaction, the reaction mixture was washed with 2N hydrochloric acid, 3% aqueous sodium hydrogen-carbonate solution and water in this order and then dried over anhydrous magnesium sulfate. The solvent was removed by distillation under reduced pressure. The residue obtained was purified by a column chromatography (eluant; chloroform) to obtain 12.00 g (yield: 90.2%) of oily N-acetylglycyl phytyl.

IR (neat) cm$^{-1}$: 3280, 2920, 2860, 1747, 1650.

NMR (CDCl$_3$) δ value: 0.86 (12H, d, J=5.5Hz), 1.00–1.60 (19H, m), 1.69 (3H, s), 1.85–2.30 (5H, m), 4.01 (2H, d, J=4.9Hz), 4.66 (2H, d, J=7.3Hz), 5.39 (1H, t, J=7.1Hz), 6.23 (1H, bs).

In the same manner, the compounds of Table 4 were obtained.

TABLE 4

| No. of Reference Example | Name of compound | IR (neat) cm$^{-1}$: | NMR (CDCL$_3$) δ value: |
|---|---|---|---|
| 23 | N-acetyl-L-methionyl phytyl | 2910, 2850, 1740, 1650 | 0.86(12H, d, J=5.5Hz), 1.00–1.55(19H, m), 1.71 (3H, s), 1.81–2.28(10H, m), 2.28–2.70(2H, m), 4.80(2H, d, J=7.0Hz), 5.34(1H, t, J=7.0Hz), 6.70(1H, d, J=10.0Hz) |
| 24 | N,N-dimethyl-glycylphytyl | 2920, 2850, 1740 | 0.86(12H, d, J=5.6Hz), 1.05–1.60(19H, m), 1.70 (3H, s), 1.90–2.30(2H, m), 2.35(6H, s), 3.15 (2H, s), 4.64(2H, d, J=7.0Hz), 5.36(1H, t, J=6.4Hz) |
| 25 | N-acetyl-L-prolylphytyl | 2920, 2860, 1740, 1650 | 0.86(12H, d, J=5.5Hz), 1.00–1.60(19H, m), 1.70 (3H, s), 1.82–2.40(9H, m), 3.30–3.80(2H, m), 4.20–4.80(3H, m), 5.38(1H, t, J=6.8Hz) |
| 26 | N-acetyl-D,L-valylphytyl | 3280, 2920, 2860, 1730, 1650 | 0.50–1.05(18H, m), 1.05–1.60(19H, m), 1.71(3H, s), 1.82–2.50(6H, m), 4.30–4.80(3H, m), 5.34 (1H, t, J=6.8Hz), 6.32(1H, d, J=10.5Hz) |

REFERENCE EXAMPLE 27

A solution of 5.00 g of N-trichloroethoxycarbonylglycine and 6.10 g of 4-(N,N-dimethylamino)pyridine dissolved in 35 ml of methylene chloride was cooled to −50° C. Thereinto was dropped 2.10 g of methanesulfonyl chloride. After the completion of the dropping, the resulting mixture was stirred at the same temperature for 1 hour. Thereinto was dropped 4.93 g of phytol at the same temperature, after which the temperature of the reaction mixture was elevated to room temperature in 6 hours. The reaction mixture was then washed with 2N hydrochloric acid, 3% aqueous sodium hydrogencarbonate solution and water in this order and then dried over anhydrous magnesium sulfate. The solvent was removed by distillation under reduced pressure. The residue obtained was dissolved in 86 ml of tetrahydrofuran. To the resulting solution were added 86 ml of 0.5N aqueous potassium primary phosphate solution and 13.40 g of zinc powder. The resulting mixture was stirred for 2 hours at room temperature. The reaction mixture was filtered. The filtrate was concentrated under reduced pressure. To the residue obtained was added 30 ml of ethyl acetate. The resulting mixture was washed with 2N hydrochloric acid and then dried over anhydrous magnesium sulfate. Into the resulting solution was introduced hydrogen chloride gas. Then, the solvent was removed from the resulting solution by distillation under reduced pressure to obtain 5.80 g (yield: 90%) of oily glycylphytyl hydrochloride.

IR (neat) cm$^{-1}$: 3400, 2920, 2860, 1745.

NMR (CDCl$_3$) δ value: 0.86 (12H, d, J=5.5Hz), 1.00–1.60 (19H, m), 1.68 (3H, s), 1.95–2.12 (2H, m), 3.99 (2H, s), 4.61 (2H, d, J=6.6Hz), 5.30 (1H, t, J=6.6Hz).

REFERENCE EXAMPLE 28

D,L-valylphytyl hydrochloride was obtained in the same manner as in Reference Example 27.

IR (neat) cm$^{-1}$: 2910, 2850, 1730.

NMR (CDCl$_3$) δ value: 0.50–1.5 (18H, m), 1.05–1.60 (19H, m), 1.71 (3H, m), 1.82–2.50 (3H, m), 4.00 (1H, s), 4.70 (2H, d, J=7.0Hz), 5.32 (1H, t, J=7.0Hz), 8.30 (2H, s).

REFERENCE EXAMPLE 29

4.5 g of methyl iodide was added to a solution of 10.0 g of N,N-dimethylglycylphytyl dissolved in 30 ml of methylene chloride. The resulting mixture was stirred for 1 hour at room temperature. After the completion of the reaction, the solvent was removed by distillation under reduced pressure to obtain 12.0 g (yield: 88%) of oily phytyl α-trimethylammonioacetate iodide.

IR (neat) cm$^{-1}$: 2910, 2850, 1735.

NMR (CDCl$_3$) δ value: 0.89 (12H, d, J=5.5Hz), 1.00–1.65 (19H, m), 1.71 (3H, s), 1.90–2.30 (2H, m), 3.74 (9H, s), 4.70–5.10 (4H, m), 5.34 (1H, t, J=6.1Hz).

REFERENCE EXAMPLE 30

10.0 g of phytyl chloride was dropped into a solution of 2.0 g of sodium methoxide dissolved in 70 ml of methanol. The resulting mixture was stirred for 4 hours at 60° C. After the completion of the reaction, the reaction mixture was concentrated under reduced pressure. The residue obtained was dissolved in 30 ml of ethyl acetate, and the resulting solution was washed with water. The solution was dried over anhydrous magnesium sulfate and the solvent was removed by distillation under reduced pressure. The residue thus obtained was subjected to distillation (b.p.: 148°–150° C., 1.5 mmHg) to obtain 9.4 g (yield: 95%) of oily methyl phytyl ether.

IR (neat) cm$^{-1}$: 2920, 2850, 1095.

NMR (CDCl$_3$) δ value: 0.86 (12H, d, J=5.5Hz), 1.00–1.60 (19H, m), 1.74 (3H, s), 1.85–2.30 (2H, m), 3.30 (3H, s), 3.92 (2H, d, J=6.7Hz), 5.34 (1H, t, J=6.7Hz).

In the same manner, the compounds of Table 5 were obtained.

TABLE 5

| No. of Reference Example | Name of compound | IR (neat) cm$^{-1}$: | NMR (CDCl$_3$) δ value: |
|---|---|---|---|
| 31 | Ethyl phytyl ether | 2920, 2860, 1100 | 0.86(12H, d, J=5.5Hz), 1.00–1.60(22H, m), 1.65 (3H, s), 1.86–2.20(2H, m), 3.47(2H, q,) J=7.0Hz), 3.96(2H, d, J=6.7Hz), 5.34(1H, t, J=6.7Hz) |
| 32 | Isopropyl phytyl ether | 2920, 2860, 1060 | 0.86(18H, m), 1.00–1.60(19H, m), 1.64(3H, s), 1.82–2.40(2H, m), 3.20–3.85(1H, m), 3.85(2H, d, J=6.7Hz), 5.35(1H, t, J=6.7Hz) |

TABLE 5-continued

| No. of Reference Example | Name of compound | IR (neat) cm$^{-1}$: | NMR (CDCl$_3$) δ value: |
|---|---|---|---|
| 33 | t-Butyl phytyl ether | 2920, 2860, 1060 | 0.86(12H, d, J=5.5Hz), 1.00–1.60(28H, m), 1.65 (3H, s), 1.85–2.30(2H, m), 3.89(2H, d, J=6.7Hz), 5.30(1H, t, J=6.7Hz) |

REFERENCE EXAMPLE 34

0.84 g of sodium hydride was added to a solution of 2.40 g of ethylmercaptan dissolved in 30 ml of N,N-dimethylformamide. Thereinto was dropped 10.00 g of phytyl chloride at 40° C. The resulting mixture was stirred at the same temperature for 3 hours. After the completion of the reaction, the resulting mixture was concentrated under reduced pressure. The residue obtained was dissolved in 30 ml of ethyl acetate. The resulting solution was washed with 1N hydrochloric acid, 3% aqueous sodium hydrogencarbonate solution and water in this order and then dried over anhydrous magnesium sulfate. The solvent was removed by distillation under reduced pressure. The residue obtained was purified by a column chromatography (eluant: n-hexane:ethyl acetate=9:1) to obtain 10.00 g (yield: 92%) of oily ethyl phytyl thioether.

IR (neat) cm$^{-1}$: 2920, 2860.

NMR (CDCl$_3$) δ value: 0.86 (12H, d, J=5.6Hz), 1.00–1.60 (22H, m), 1.63 (3H, s), 1.80–2.20 (2H, m), 2.20–2.80 (2H, m), 3.14 (2H, d, J=7.5Hz), 5.30 (1H, t, J=7.5Hz).

REFERENCE EXAMPLE 35

5.1 g of m-chloroperbenzoic acid was added to a solution of 10.0 g of ethyl phytyl thioether dissolved in 30 ml of methylene chloride. The resulting mixture was stirred for 2 hours at room temperature. After the completion of the reaction, the reaction mixture was washed with 2% aqueous sodium hdyrogensulfite solution, 3% aqueous sodium hydrogencarbonate solution and water in this order and then dried over anhydrous magnesium sulfate. The solvent was removed by distillation under reduced pressure. The residue obtained was purified by a column chromatography (eluant: n-hexane:ethyl acetate =9:1) to obtain 9.4 g (yield: 90%) of oily ethyl phytyl sulfoxide.

IR (neat) cm$^{-1}$: 2910, 2860, 1050.

NMR (CDCl$_3$) δ value: 0.86 (12H, d, J=5.5Hz), 1.00–1.60 (22H, m), 1.72 (3H, s), 1.84–2.30 (2H, m), 2.30–3.00 (2H, m), 3.45 (2H, d, J=7.9Hz), 5.27 (1H, t, J=7.9Hz).

REFERENCE EXAMPLE 36

10.2 g of m-chloroperbenzoic acid was added to a solution of 10.0 g of ethyl phytyl thioether dissolved in 50 ml of methylene chloride. The resulting mixture was stirred for 2 hours at room temperature. After the completion of the reaction, the reaction mixture was washed with 2% aqueous sodium hdyrogensulfite solution, 3% aqueous sodium hydrogencaerbonate solution and water in this order and then dried over anhydrous magnesium sulfate. The solvent was removed by distillation under reduced pressure. The residue obtained was purified by a column chromatography (eluant: benzene) to obtain 10.0 g (yield: 91%) of oily ethyl phytyl sulfone.

IR (neat) cm$^{-1}$: 2910, 2850, 1305, 1120.

NMR (CDCl$_3$) δ value: 0.86 (12H, d, J=5.5Hz), 1.00–1.60 (22H, m), 1.72 (3H, s), 1.90–2.30 (2H, m), 2.30–3.20 (2H, m), 3.68 (2H, d, J=7.9Hz), 5.30 (1H, t, J=7.9Hz).

REFERENCE EXAMPLE 37

2.0 g of methyl isocyanate was added to a solution of 5.0 g of phytol dissolved in 15 ml of methylene chloride. The resulting mixture was refluxed for 6 hours. After the completion of the reaction, the reaction mixture was concentrated under reduced pressure. The residue obtained was purified by a column chromatography (eluant: benzene) to obtain 5.5 g (yield: 99.2%) of oily phytyl N-methylcarbamate.

IR (neat) cm$^{-1}$: 2910, 2850, 1305, 1120.

NMR (CDCl$_3$) δ value: 0.86 (12H, d, J=5.5Hz), 1.00–1.60 (19H, m), 1.72 (3H, s), 1.82–2.28 (2H, m), 3.65 (3H, s), 4.57 (2H, d, J=6.7Hz), 5.34 (1H, t, J=6.7Hz).

REFERENCE EXAMPLE 38

A solution of 5.0 g of 3,7,11,15-tetramethyl-2-hexadecenoic acid and 4.3 g of 4-(N,N-dimethylamino)-pyridine dissolved in 50 ml of methylene chloride was cooled to −50° C. Thereinto was dropped 1.8 g of methanesulfonyl chloride. After the completion of the dropping, the resulting mixture was stirred at the same temperature for 1 hour. Thereinto was dropped 3.2 g of 2,2-dimethyl-1,3-dioxolane-4-methanol at the same temperature. After the completion of the dropping, the temperature of the reaction mixture was elevated to room temperature in 6 hours. After the completion of the reaction, the reaction mixture was washed with 1N hydrochloric acid, 3% aqueous sodium hydrogencarbonate solution and water in this order, and the solvent was removed by distillation under reduced pressure. The residue obtained was dissolved in 50 ml of acetonitrile. To the resulting solution was added 5 ml of 2N hydrochloric acid. The resulting mixture was stirred for 5 hours at room temperature. The reaction mixture was neutralized with triethylamine, and then concentrated under reduced pressure. The residue obtained was dissolved in 20 ml of ethyl acetate. The resulting solution was washed with 1N hydrochloric acid, 3% asqueous sodium hydrogencarbonate solution and water in this order and then dried over anhydrous magnesium sulfate. The solvent was removed by distillation under reduced pressure. The redsidue obtianed was purified by a column chromatography (eluant: benzene) to obtain 6.0 g (yield: 96.7%) of oily glyceryl 3,7,11,15-tetramethyl-2-hexadecenoate.

IR (neat) cm$^{-1}$: 3300, 2920, 2860, 1720, 1640.

NMR (CDCl$_3$) δ value: 0.86 (12H, d, J=5.5Hz), 0.99–1.70 (21H, m), 2.25 (3H, s), 3.50–4.40 (7H, m), 5.70 (1H, s).

REFERENCE EXAMPLE 39

A solution of 5.0 g of 3,7,11,15-tetramethyl-2-hexadecenoic acid and 4.3 g of 4-(N,N-dimethylamino)-pyridine dissolved in 50 ml of methylene chloride was cooled to −50° C. Thereinto was dropped 1.8 g of methanesulfonyl chloride. After the completion of the dropping, the resulting mixture was stirred for 1 hour at the same temperature. Then, 2 ml of ethyl alcohol was dropped thereinto at the same temperature. After the completion of the dropping, the temperature of the reaction mixture was elevated to room temperature in 6 hours. After the completioon of the reaction, the reaction mixture was washed with 1N hydrochloric acid, 3% aqueous sodium hdyrogencarbonate soilution and water in this order and then dried over magnesium sulfate. The solvent was removed by distillation under reduced pressure. The residue obtained was subjected to distillation (b.p.: 163°-165° C., 0.5 mmHg) to obtion 5.0 g (yield: 91.7%) of oily ethyl 3,7,11,15-tetramethyl-2-hexadecenoate.

IR (neat) cm$^{-1}$: 2930, 2870, 1722, 1650.

NMR (CDCl$_3$) δ value: 0.86 (12H, d, J=5.5Hz), 0.99-1.77 (24H, m), 2.25 (3H, s), 4.15 (2H, q, J=7.0Hz), 5.65 (1H, s).

REFERENCE EXAMPLE 40

6.6 g of sodium cyanate was added to a solution of 10.0 g of phytol dissolved in 50 ml of acetic acid, in small portions. The resulting mixture was stirred for 6 hours at room temperature. After the completion of the reaction, the reaction mixture was concentrated under reduced pressure. The residue obtained was dissolved in 50 ml of ethyl acetate. The solution was washed with 3% aqueous sodium hydrogen-carbonate solution and water in this order and then dried over anhydrous magnesium sulfate. The solution was concentrated under reduced pressure. The residue obtained was purified by a column chromatography (eluant: benzene) to obtain 10.0 g (yield: 87%) of oily phytyl carbamate.

IR (neat) cm$^{-1}$: 3320, 2910, 2850, 1720.

NMR (CDCl$_3$) δ value: 0.86 (12H, d, J=5.5Hz), 1.00-1.60 (19H, m), 1.73 (3H, m), 1.80-2.30 (2H, m), 4.57 (2H, d, J=7.0Hz), 5.34 (1H, d, J=7.0Hz).

The following Examples illustrate forms and composition (% by weight) of the hair-restorer of this invention. The following forms and compositions are applied to mammalian skin. It should not be construed that this invention be restricted to the Examples.

| Component | Amount (wt. %) |
|---|---|
| Example 1 Hair lotion | |
| 95% Ethanol | 80.0 |
| Phytyl acetyllactate | 3.0 |
| Pyrrolidonecarboxylic acid | 0.5 |
| Propylene glycol | 5.0 |
| Lavender oil | 0.1 |
| Purified water | 11.4 |
| Example 2 Hair lotion | |
| 95% Ethanol | 80.0 |
| Phytyl acetate | 3.0 |
| Pyrrolidonecarboxylic acid | 0.5 |
| Propylene glycol | 5.0 |
| Tocopheryl acetate | 1.0 |
| Lecithin (Lecinol Y-10E, product of Nikko Chemicals) | 1.0 |
| Lavender oil | 0.1 |
| Purified water | 9.4 |
| Example 3 Hair cream | |
| Phytyl acetate | 3.0 |
| Olive oil | 5.0 |
| Liquid paraffin | 50.0 |
| Bees wax | 1.0 |
| Lecithin (Lecinol Y-10E, product of Nikko Chemicals) | 1.0 |
| Polyoxyethylene hardened castor oil (50E.O) | 3.0 |
| Purified water | 37.0 |
| Example 4 Hair rinse | |
| Stearyltrimethylammonium chloride | 1.5 |
| Distearyldimethylammonium chloride | 0.5 |
| Cetyl alcohol | 1.5 |
| Phytyl nicotinate | 3.0 |
| Sodium laurylsulfate | 3.0 |
| Liquid paraffin | 1.0 |
| Purified water | 89.5 |
| Example 5 Hair lotion | |
| 95% Ethanol | 80.0 |
| Methyl phytyl ether | 3.0 |
| Pyrrolidonecarboxylic acid | 0.5 |
| Propylene glycol | 5.0 |
| Lavender oil | 0.1 |
| Purified water | 11.4 |
| Example 6 Hair lotion | |
| 95% Ethanol | 80.0 |
| Glyceryl 3,7,11,15-tetramethyl-2-hexadecenoate | 3.0 |
| Pyrrolidonecarboxylic acid | 0.5 |
| Propylene glycol | 5.0 |
| Tocopheryl acetate | 1.0 |
| Lecithin (Lecinol Y-10E, product of Nikko Chemicals) | 1.0 |
| Lavender oil | 0.1 |
| Purified water | 9.4 |
| Example 7 Hair cream | |
| Ethyl phytyl ether | 3.0 |
| Olive oil | 5.0 |
| Liquid paraffin | 50.0 |
| Bees wax | 1.0 |
| Lecithin (Lecinol Y-10E, product of Nikko Chemicals) | 1.0 |
| Polyoxyethylene hardened castor oil (50E.O) | 3.0 |
| Purified water | 37.0 |
| Example 8 Hair rinse | |
| Stearyltrimethylammonium chloride | 1.5 |
| Distearyldimethylammonium chloride | 0.5 |
| Cetyl alcohol | 1.5 |
| Glyceryl 3,7,11,15-tetramethyl-2-hexadecenoate | 3.0 |
| Sodium laurylsulfate | 3.0 |
| Liquid paraffin | 1.0 |
| Purified water | 89.5 |
| Example 9 Hair lotion | |
| 95% Ethanol | 80.00 |
| Phytol | 3.00 |
| Propylene glycol | 1.00 |
| Ceramide | 0.01 |
| Hinokitiol | 0.05 |
| Laventer oil | 0.10 |
| Purified water | 15.84 |

What is claimed is:

1. A process for increasing the rate of hair growth in mammalian species, comprising applying to mammalian skin an effective amount of a compound selected from the group consisting of:
   a. phytol
   b. isophytol
   c. phytantriol
   d. phytyl nicotinate
   e. phytyl propionate
   f. phytyl isobutyrate
   g. phytyl 3,4,5-trimethoxybenzoate
   h. phytyl acetate
   i. phytyl acetyl lactate
   j. phytyl pivalate
   k. phytyl formyl lactate l. phytyl lactate
m. N-acetylglycyl phytyl
n. N,N-dimethylglycyl phytyl
o. D,L-vinyl phytyl
p. phytyl α-trimethylammonium acetate
q. methyl phytyl ether
r. ethyl phytyl ether
s. isopropyl phytyl ether
t. t-butyl phytyl ether
u. phytyl N-methylcarbamate
v. glycerol 3,7,11,15-tetramethyl-2-hexadecenoate
w. ethyl 3,7,11,15-tetramethyl-2-hexadecenoate
x. monophytyl succinate
y. phytyl ethoxypropionate
z. methyl phytyl succinate
a'. isophytyl acetate
b'. N-acetyl-L-methionyl phytyl
c'. N-acetyl-D-valyl phytyl
d'. ethyl phytyl thioether
e'. ethyl phytyl sulfoxide
f'. ethyl phytyl sulfone and
g'. phytyl carbamate.

2. The process according to claim 1, wherein the compound is phytol.

3. The process according to claim 1, wherein the compound is isophytol.

4. The process according to claim 1, wherein the compound is phytantriol.

5. The process according to claim 1, wherein the compound is phytyl nicotinate.

6. The process according to claim 1, wherein the compound is phytyl 3,4,5-trimethoxybenzoate.

7. The process according to claim 1, wherein the compound is monophytyl succinate.

8. The process according to claim 1, wherein the compound is phytyl ethoxypropionate.

9. The process according to claim 1, wherein the compound is methyl phytyl succinate.

10. The process according to claim 1, wherein the compound is isophytyl acetate.

11. The process according to claim 1, wherein the compound is N-acetyl-L-methionyl phytyl.

12. The process according to claim 1, wherein the compound is N-acetyl-D-valyl phytyl.

13. The process according to claim 1, wherein the compound is ethyl phytyl thioether.

14. The process according to claim 1, wherein the compound is ethyl phytyl sulfoxide.

15. The process according to claim 1, wherein the compound is ethyl phytyl sulfone.

16. The process according to claim 1, wherein the compound is phytyl carbamate.

17. A process for increasing the rate of hair growth in mammalian species, comprising applying to mammalian skin an effective amount of a compound selected from the group consisting of:
A. phytol
B. isophytol
C. phytyl nicotinate
D. phytyl propionate
E. phytyl isobutyrate
F. phytyl 3, 4, 5-trimethyl benzoate
G. phytyl acetate
H. phytyl acetyl lactate
I. phytyl pivalate
J. monophytyl succinate
K. phytyl ethoxy propionate
L. methyl phytyl succinate
M. isophytyl acetate.

18. A process for increasing the rate of hair growth in mammalian species, comprising applying to mammalian skin an effective amount of a compound selected from the group consisting of:
A. phytol
B. isophytol
C. phytyl nicotinate
D. phytyl propionate
E. phytyl isobutyrate
F. phytyl 3, 4, 5-trimethoxybenzoate
G. phytyl acetate
H. phytyl acetyl lactate
I. phytyl pivalate
J. phytyl formyl lactate
K. phytyl lactate
L. N-acetylglycyl phytyl
M. N,N-dimethylglycyl phytyl
N. D,L-valyl phytyl
O. phytyl α-trimethylammonium acetate
P. methyl phytyl ether
Q. ethyl phytyl ether
R. isopropyl phytyl ether
S. t-butyl phytyl ether
T. phytyl N-methylcarbamate
U. glycerol 3,7,11,15-tetramethyl-2-hexadecenoate
V. ethyl 3,7,11,15-tetramethyl-2-hexadecenoate
W. monophytyl succinate
X. phytyl ethoxypropionate
Y. methyl phytyl succinate
Z. isophytyl acetate
a'. N-acetyl-L-methionyl phytyl
b'. N-acetyl-D-valyl phytyl
c'. ethyl phytyl thioether
d'. ethyl phytyl sulfoxide
e'. ethyl phytyl sulfone and
f'. phytyl carbamate.

19. The process according to claim 1, wherein the compound is phytyl propionate.

20. The process according to claim 1, wherein the compound is phytyl isobutyrate.

21. The process according to claim 1, wherein the compound is phytyl acetate.

22. The process according to claim 1, wherein the compound is phytyl acetyllactate.

23. The process according to claim 1, wherein the compound is phytyl pivalate.

24. The process according to claim 1, wherein the compound is phytyl formyllactate.

25. The process according to claim 1, wherein the compound is phytyl lactate.

26. The process according to claim 1, wherein the compound is N-acetylglycyl phytyl.

27. The process according to claim 1, wherein the compound is N,N-dimethylglycyl phytyl.

28. The process according to claim 1, wherein the compound is D,L-valyl phytyl.

29. The process according to claim 1, wherein the compound is phytyl α-trimethylammonioacetate.

30. The process according to claim 1, wherein the compound is methyl phytyl ether.

31. The process according to claim 1, wherein the compound is ethyl phytyl ether.

32. The process according to claim 1, wherein the compound is isopropyl phytyl ether.

33. The process according to claim 1, wherein the compound is t-butyl phytyl ether.

34. The process according to claim 1, wherein the compound is phytyl N-methylcarbamate.

35. The process according to claim 1, wherein the compound is glycerol 3,7,11,15-tetramethyl-2-hexadecenoate.

36. The process according to claim 1, wherein the compound is ethyl 3,7,11,15-tetramethyl-2-hexadecenoate.

37. The process according to any one of claims 19-36 and 1-16, wherein the compound is in association with a topical pharamaceutical carrier selected from the group consisting of powder, jelly, hair rinse, ointment, hair lotion, paste, hair cream, hair tonic, hair spray and hair aerosol.

38. The process according to claim 37, wherein compound is present in an amount of 0.1 to 10% by weight.

* * * * *

UNITED STATES PATENT AND TRADEMARK OFFICE
CERTIFICATE OF CORRECTION

PATENT NO.   : 5,236,950
DATED        : August 17, 1993
INVENTOR(S)  : Hajime Aoyama et al.

It is certified that error appears in the above-indentified patent and that said Letters Patent is hereby corrected as shown below:

On the title page, Item [30], should read: --Feb. 18, 1988 [JP]   Japan............63-33968

Jun. 3, 1988  [JP]   Japan............63-136824

Jan. 27, 1989 [JP]   Japan............1-18134

Jan. 27, 1989 [JP]   Japan............1-18135

Feb. 2, 1989  [JP]   Japan............1-22560--

Signed and Sealed this

Twenty-ninth Day of March, 1994

Attest:

BRUCE LEHMAN

Attesting Officer      Commissioner of Patents and Trademarks